(12) United States Patent
Suzuki et al.

(10) Patent No.: US 8,231,592 B2
(45) Date of Patent: Jul. 31, 2012

(54) DISPOSABLE DIAPER

(75) Inventors: Sachiyo Suzuki, Kagawa-ken (JP);
Toshifumi Otsubo, Kagawa-ken (JP)

(73) Assignee: Unicharm Corporation, Ehime (JP)

( * ) Notice: Subject to any disclaimer, the term of this patent is extended or adjusted under 35 U.S.C. 154(b) by 1031 days.

(21) Appl. No.: 11/142,384

(22) Filed: Jun. 2, 2005

(65) Prior Publication Data

US 2005/0273073 A1    Dec. 8, 2005

(30) Foreign Application Priority Data

Jun. 3, 2004  (JP) ................ 2004-165371

(51) Int. Cl.
*A61F 13/15* (2006.01)
*A61F 13/20* (2006.01)

(52) U.S. Cl. ............... 604/385.101; 604/385.01

(58) Field of Classification Search .. 604/385.24–385.3, 604/385.1, 385.2, 385 R, 385 A, 384, 385.21, 604/385.01, 385.08, 385.19, 348, 397–98; 128/155–56, 287

See application file for complete search history.

(56) References Cited

U.S. PATENT DOCUMENTS

| | | | | |
|---|---|---|---|---|
| 2,110,867 A | * | 3/1938 | Castles | 428/89 |
| 3,332,828 A | * | 7/1967 | Faria et al. | 428/17 |
| 3,367,333 A | * | 2/1968 | Scheier | 604/375 |
| 3,511,740 A | * | 5/1970 | Sanders | 428/92 |
| 3,523,861 A | * | 8/1970 | Newman | 442/399 |
| 3,665,922 A | | 5/1972 | Skora | |
| 3,666,608 A | * | 5/1972 | Mattes | 428/81 |
| 4,042,453 A | * | 8/1977 | Conway et al. | 162/108 |
| 4,576,848 A | * | 3/1986 | Dillon et al. | 428/89 |
| 4,622,253 A | * | 11/1986 | Levy | 428/91 |
| 4,695,278 A | | 9/1987 | Lawson | |
| 4,895,568 A | | 1/1990 | Enloe | |
| 5,108,820 A | * | 4/1992 | Kaneko et al. | 428/198 |
| 5,167,653 A | | 12/1992 | Igaue et al. | |
| 5,295,986 A | | 3/1994 | Zehner et al. | |
| 5,334,176 A | | 8/1994 | Buenger et al. | |
| 5,460,622 A | * | 10/1995 | Dragoo et al. | 604/378 |
| 5,482,007 A | * | 1/1996 | Kumlin | 119/169 |
| 5,575,785 A | | 11/1996 | Gryskiewicz et al. | |
| 5,620,431 A | | 4/1997 | LeMahieu et al. | |
| 5,670,110 A | * | 9/1997 | Dirk et al. | 264/504 |

(Continued)

FOREIGN PATENT DOCUMENTS

EP    0 978 265 A2    2/2000

(Continued)

OTHER PUBLICATIONS

Translation of Fr 2713083 (equivalent to WO 95/15138).*

(Continued)

*Primary Examiner* — Tatyana Zalukaeva
*Assistant Examiner* — Susan Su
(74) *Attorney, Agent, or Firm* — Lowe, Hauptman, Ham & Berner, LLP (57) ABSTRACT

A disposable diaper is provided with a barrier adapted to prevent body fluid from freely flowing in a back-and-forth direction of the diaper so that such barrier can be reliably held in close contact with the wearer's skin. The barrier stands in the way of body fluid flowing in the back-and-forth direction of the diaper and the barrier is provided in the form of an assembly of nonwoven fabric strips.

15 Claims, 8 Drawing Sheets

U.S. PATENT DOCUMENTS

| | | | |
|---|---|---|---|
| 5,695,487 A | 12/1997 | Cohen et al. | |
| 5,906,876 A * | 5/1999 | Conway | 428/89 |
| 6,022,338 A | 2/2000 | Putzer | |
| 6,152,905 A * | 11/2000 | Osborn et al. | 604/378 |
| 6,156,024 A | 12/2000 | Schulte et al. | |
| 6,221,460 B1 | 4/2001 | Weber et al. | |
| 6,222,092 B1 * | 4/2001 | Hansen et al. | 604/378 |
| 6,258,997 B1 | 7/2001 | Johansson et al. | |
| 6,413,248 B1 | 7/2002 | Mizutani | |
| 6,436,081 B1 | 8/2002 | Wada et al. | |
| 6,482,195 B1 | 11/2002 | Kumasaka | |
| 6,521,813 B1 | 2/2003 | Chihani | |
| 6,639,119 B2 * | 10/2003 | Roe et al. | 604/367 |
| 6,706,029 B1 | 3/2004 | Suzuki et al. | |
| 6,733,610 B2 | 5/2004 | Mizutani et al. | |
| 6,770,581 B1 * | 8/2004 | DeMott et al. | 442/312 |
| 6,890,327 B2 | 5/2005 | Suzuki et al. | |
| 7,172,801 B2 | 2/2007 | Hoying et al. | |
| 2002/0029023 A1 * | 3/2002 | Furuya et al. | 604/368 |
| 2004/0131820 A1 | 7/2004 | Turner et al. | |
| 2005/0182381 A1 | 8/2005 | Suzuki et al. | |
| 2005/0273073 A1 | 12/2005 | Suzuki et al. | |

FOREIGN PATENT DOCUMENTS

| | | | |
|---|---|---|---|
| EP | 1358863 A1 | 11/2003 | |
| EP | 1716831 A1 | 11/2006 | |
| EP | 1757256 A1 | 2/2007 | |
| JP | 2174845 A | 7/1990 | |
| JP | 3218752 A | 9/1991 | |
| JP | 467864 | 3/1992 | |
| JP | 1996-322878 | 12/1996 | |
| JP | 928732 A | 2/1997 | |
| JP | 928732 A * | 4/1997 | |
| JP | 1057409 A * | 3/1998 | |
| JP | 1998-192338 | 7/1998 | |
| JP | 200245396 A | 2/2002 | |
| JP | 2002-315776 | 10/2002 | |
| JP | 2002-345887 A | 12/2002 | |
| JP | 2004-248769 A | 9/2004 | |
| JP | 2005-342203 A | 12/2005 | |
| WO | 92/14429 A1 | 9/1992 | |
| WO | 95/15138 A1 | 6/1995 | |
| WO | 9602216 A1 | 2/1996 | |
| WO | 03032882 A1 | 4/2003 | |
| WO | 2004/058497 A1 | 7/2004 | |

OTHER PUBLICATIONS

Merriam-webster OnLine definitions of "strip". "monolithic", "fabric" and "cloth".*

Derwent Abstract, KR2007013398, Feb. 15, 2008.*

European search report for EP application No. 05710309.5 issued Jun. 18, 2009.

Search Report for corresponding European Application No. 05751450 issued Jan. 15, 2010.

* cited by examiner

DISPOSABLE DIAPER

RELATED APPLICATIONS

The present application is based on, and claims priority from, Japanese Application Number 2004-165371, filed Jun. 3, 2004, the disclosure of which is hereby incorporated by reference herein in its entirety.

BACKGROUND OF THE INVENTION

This invention relates to a generally disposable diaper and particularly to such a diaper provided with a barrier adapted to stand in the way of body fluid moving on a body fluid absorbent panel in a back-and-forth direction of the diaper.

The conventional disposable diaper includes a crotch covering region, a front waist covering region, a rear waist covering region, and a body fluid absorbent panel extending over the crotch covering region and into the front and rear waist covering regions. A barrier extending in the crotch covering region across a body fluid absorbent panel stands in the way of body fluid flowing on the body fluid absorbent panel in a back-and-forth direction of the diaper.

For example, a diaper disclosed in Japanese Unexamined Patent Application Publication No. 1996-322878 (Reference 1) is provided along transversely opposite side edges of the diaper with a pair of leak-barrier cuffs adapted to be elastically stretchable in the back-and-forth direction and, in the crotch covering region of the diaper, with a flap extending between these leak-barrier cuffs in the transverse direction of the diaper. The flap is formed from folding a nonwoven fabric or plastic film in a Z- or inverted Z-shape wherein a bottom of the flap corresponding to the bottom of Z-shape is bonded to a topsheet of the diaper and a top of the flap corresponding to the top of Z-shape is provided with an elastic member extending in the transverse direction of the diaper and bonded in a stretched state to the top of the flap. Longitudinally opposite ends of this top of the flap are bonded to inner surfaces of the respective leak-barrier cuffs. The leak-barrier cuffs elastically contract in the back-and-forth direction of the diaper as the diaper is put on the wearer and curves along the back-and-forth direction whereupon the leak-barrier cuffs rise up above the topsheet and simultaneously the flap having the transversely opposite ends bonded to the respective leak-barrier cuffs rises up above the topsheet. In such a state, the flap functions as a barrier adapted to prevent loose passage from flowing toward the front waist covering region and to prevent urine from flowing toward the rear waist covering region. The top of the flap provided with the elastic member bonded in a stretched state thereto is adapted to be elastically pressed against the diaper wearer's skin.

A disposable wearing article disclosed in Japanese Unexamined Patent Application Publication No. 1998-192338 (Reference 2) includes barrier means against a flow of bodily discharges. The barrier means extends above respective surfaces of front and rear waist covering regions or at least the surface of the rear waist covering region adapted to come in contact with the wearer's skin in a transverse direction of the article. This barrier means protuberates from the topsheet surface at least by 2 mm and comprises the topsheet and a pad member having an elastic compression recovery factor higher than those of the topsheet and a liquid-absorbent core.

Both the flap disclosed in Reference 1 and the barrier means disclosed in Reference 2 certainly intend to prevent bodily discharges such as urine and loose passage from freely flowing on the topsheet of the wearing article such as the diaper in the back-and-forth direction and from soiling the wearer's skin and/or leaking out from the article. However, in the case of the flap disclosed in Reference 1, the top of this flap provided with the elastic member extending in the transverse direction of the diaper easily come in close contact with protuberant spots of the wearer's skin but not with depressed spots of the wearer's skin. Consequently, it is likely that a gap might be left between the top and the skin and bodily discharges might flow beyond the flap through such gap. Therefore it is difficult for this flap to come in close contact not only with the protuberant spots of the skin but also with the depressed spots of the skin. The barrier means disclosed in Reference 2 is provided in the form of the elastic pad member extending in the transverse direction of the waist region and it is difficult for this barrier means to come in close contact not only with the protuberant spots of the skin but also with the depressed spots of the skin.

SUMMARY OF THE INVENTION

It is an object of this invention to provide disposable diapers having a barrier adapted to prevent bodily discharges from freely flowing in a back-and-forth direction of the diaper improved so that the barrier is able to come in close contact not only with protuberant spots of the wearer's skin but also with depressed spots of the wearer's skin.

The invention is directed to a disposable diaper having a back-and-forth direction and a transverse direction being orthogonal to the back-and-forth direction. The diaper comprises a front waist covering region; a rear waist covering region; a crotch covering region; a body fluid absorbent panel at least partially wrapped with a liquid-pervious sheet and extending over the crotch covering region further into the front waist covering region as well as into the rear waist covering region, and in at least one of the crotch covering region, the front waist covering region and the rear waist covering region, a barrier extending in the transverse direction so as to stand in the way of body fluid flowing on the liquid-pervious sheet in the back-and-forth direction.

The diaper according to this invention further comprises the barrier being formed from a tufted assembly comprising a plurality of nonwoven fabric strips each having a width and a length being orthogonal to each other wherein the plurality of strips are arranged side by side with respective the widths being in alignment in the transverse direction so that the strips successively overlap one another along the respective lengths and wherein each of the strips has one end as viewed in the back-and-forth direction of the diaper fixed to the liquid-pervious sheet and the other end opposite to the one end left deformable.

The diaper according to this invention ensures that the barrier reliably comes in close contact with both the protuberant spots and the depressed spots of the wearer's skin without any significant gap left between the wearer's skin and the barrier. This is for the reason that the barrier extending across the body fluid absorbent panel comprises the assembly of nonwoven fabric strips arranged side by side can independently deform without mutual restriction as the diaper is put on the wearer's body. In this way, the diaper provided with such barrier can reliably prevent bodily discharges such as loose passage and urine from freely flowing in the back-and-forth direction.

This invention may include the following preferable embodiments.

(1) Each of the strips has the one end bonded to the liquid-pervious sheet along a line put aside from a centerline extending in the transverse direction so as to bisect a dimension of the diaper as measured in the back-and-forth direction toward the front waist covering region.

With the diaper according to this embodiment, a relatively large space is available between the anus of the diaper wearer and the barrier to retain a correspondingly large amount of loose passage because the barrier in the crotch covering region is put aside toward the front waist covering region.

(2) The barrier comprises at least one of a first barrier in which a direction of the strip defined from the one end toward the other end substantially coincides with a direction defined from the crotch covering region toward the rear waist covering region and a second barrier provided ahead of the first barrier, in which a direction of the strip defined from the one end toward the other end substantially coincides with a direction defined from the crotch covering region toward the front waist region.

Assumed that the diaper according to this embodiment has the first barrier, it will be possible for this diaper to retain loose passage between the strips and the liquid-pervious sheet and thereby to prevent loose passage from coming in contact with the wearer's skin. Assumed that the diaper has the second barrier, the topsheet wetted with urine will be covered with this second barrier and consequentially there is no anxiety that the diaper wearer might experience an uncomfortable feeling of wetness due to the topsheet wetted with urine.

(3) The nonwoven fabric contains crimped fibers.

With the diaper according to this embodiment, the crimped fiber contained in the nonwoven fabric used as the material for the strips facilitates the strips to be elastically deformed.

(4) Each of the strips is formed along its length with a plurality of folds which repetitively rise and fall.

With the diaper according to this embodiment, the presence of the folds facilitates the strips to be elastically deformed.

DETAILED DESCRIPTION OF THE PREFERRED EMBODIMENTS

Details of a disposable diaper according to this invention will be more fully understood from the description given hereunder with reference to the accompanying drawings.

Figure 1:
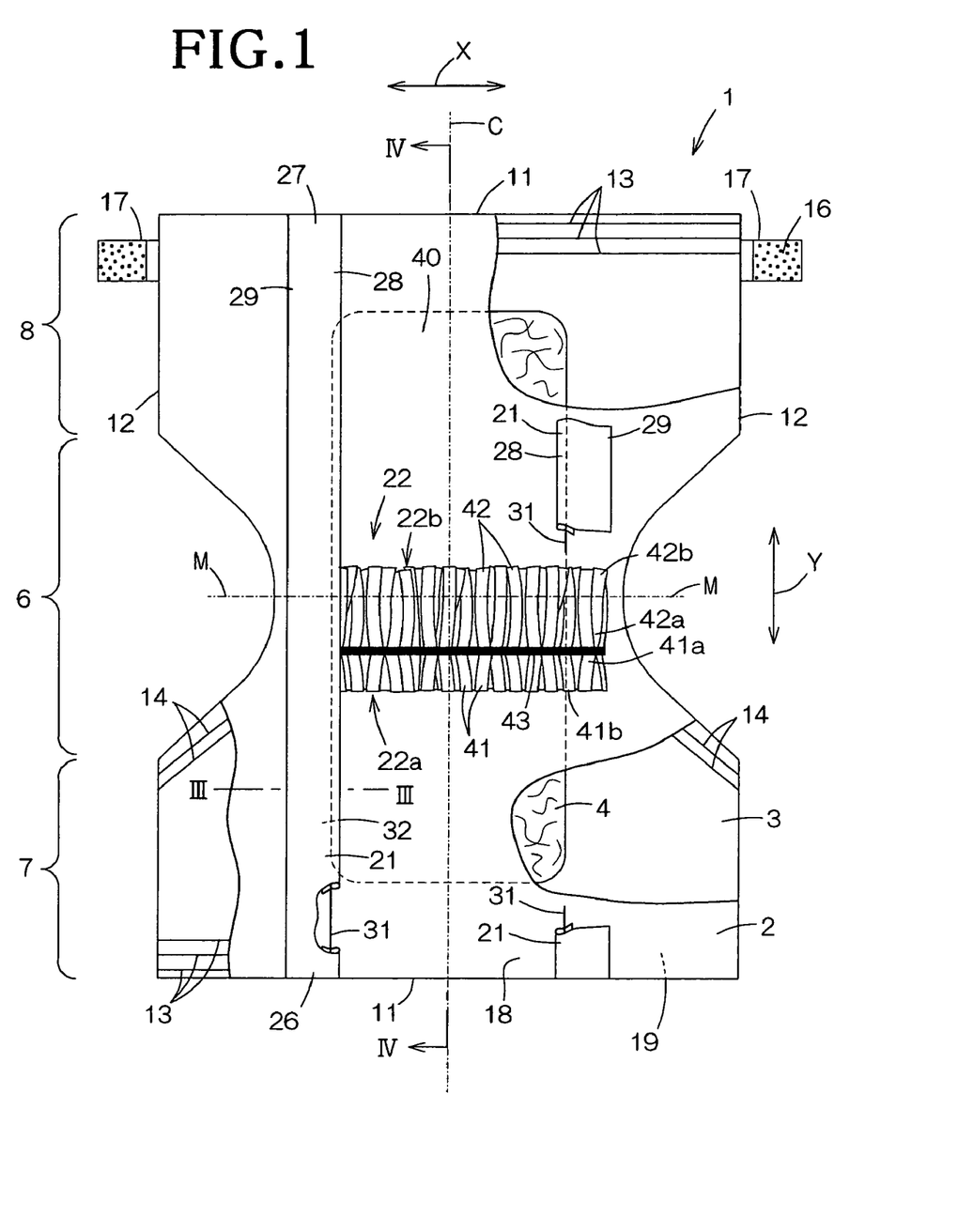
FIG. 1 is a partially cutaway plan view showing a diaper as a typical embodiment of the invention.

A disposable diaper 1 shown in FIG. 1 in a partially cutaway plan view comprises a liquid-pervious topsheet 2, a liquid-impervious backsheet 3 and a body fluid absorbent core 4 interposed between these two sheets 2, 3. The diaper 1 has a transverse direction and a back-and-forth direction are indicated by double-headed arrows X and Y being orthogonal to each other. As for configuration, the diaper 1 defines, in the back-and-forth direction Y, a crotch covering region 6, a front waist covering region 7 extending forward from the crotch covering region 6 and a rear waist covering region 8 extending rearward from the crotch covering region 6. The diaper 1 in its entirety has a generally hourglass-like planar shape contoured by a pair of ends 11 extending in the transverse direction X and a pair of side edges 12 extending in the back-and-forth direction Y. In the crotch covering region 6, the side edges 12 curve inward so as to become convex toward a centerline C-C bisecting a width of the diaper 1. The core 4 extends over the crotch covering region 6 further into the front waist covering region 7 and the rear waist covering region 8. The topsheet 2 and the backsheet 3 sandwiching the core 4 therebetween extend outward beyond a peripheral edge of the core 4 and these extensions of the top- and backsheets 2, 3 are bonded together by means of adhesives or a suitable welding technique. In each of the front and rear waist covering regions 7, 8, a plurality of waist elastic members 13 extending in the transverse direction X along the end 11 are interposed between the top- and backsheets 2, 3 and secured in a stretched state to at least one of these sheets 2, 3. In the crotch covering region 6, a plurality of leg elastic members 14 extending in the back-and-forth direction Y along the respective curving side edges 12 are interposed between the top- and backsheets 2, 3 and secured in a stretched state to at least one of these two sheets 2, 3. A pair of fastening tape strips 17 coated with pressure-sensitive adhesives 16 laterally extend from the respective side edges 12 of the rear waist covering region 8. The topsheet 2 defines an inner surface 18 of the diaper 1 facing the diaper wearer's skin and the backsheet 3 defines an outer surface 19 of the diaper 1 facing the garment. The inner surface 18 is provided with a pair of leak-barrier cuffs 21 extending in parallel to each other in the back-and-forth direction Y and a barrier 22 extending in the transverse direction X. In the diaper 1, a section in which the topsheet 2, the core 4 and the backsheet 3 are placed one upon another defines a body fluid absorbent panel 40.

The leak-barrier cuffs 21 are made of a nonwoven fabric, more preferably of a liquid-impervious nonwoven fabric and respectively have front and rear ends 26, 27 both extending in the transverse direction X, and distal and proximal side edges 28, 29 both extending in the back-and-forth direction Y. While the front ends 26, the rear ends 27 and the proximal side edges 29 are bonded to the topsheet 2 by means of adhesives or a suitable welding technique, the distal side edges 28 are left free from the topsheet 2. Sleeves 32 formed by folding back the nonwoven fabric respectively contain therein elastic members 31 so that the distal side edges 28 are elastically stretch- and contractable in the back-and-forth direction Y and cooperate with the topsheet 2 to form pockets 30 opening toward the centerline C-C (See FIG. 3).

The barrier 22 lies between a pair of the leak-barrier cuffs 21, 21 and comprises front and rear barriers 22a, 22b each comprising a plurality of strips 41, 42 made of a nonwoven fabric. Each of these strips 41, 42 has a fixed end 41a, 42a and a free end 41b, 42b wherein the fixed end 41a, 42a is directly or indirectly fixed to the topsheet 2 using a suitable welding technique along a welding line 43 extending in the transverse direction X and the free end 41b, 42b is free to be deformed. When the fixed end 41a, 42a are indirectly fixed to the topsheet 2, as used herein the term "indirectly" means that each pair of the fixed ends 41a, 41a overlapping each other, or a pair of the fixed ends overlapping each other 42a, 42a or a pair of the fixed ends 41a, 42a overlapping each other are fixed to the topsheet 2 by means of respective companions.

Figure 2:
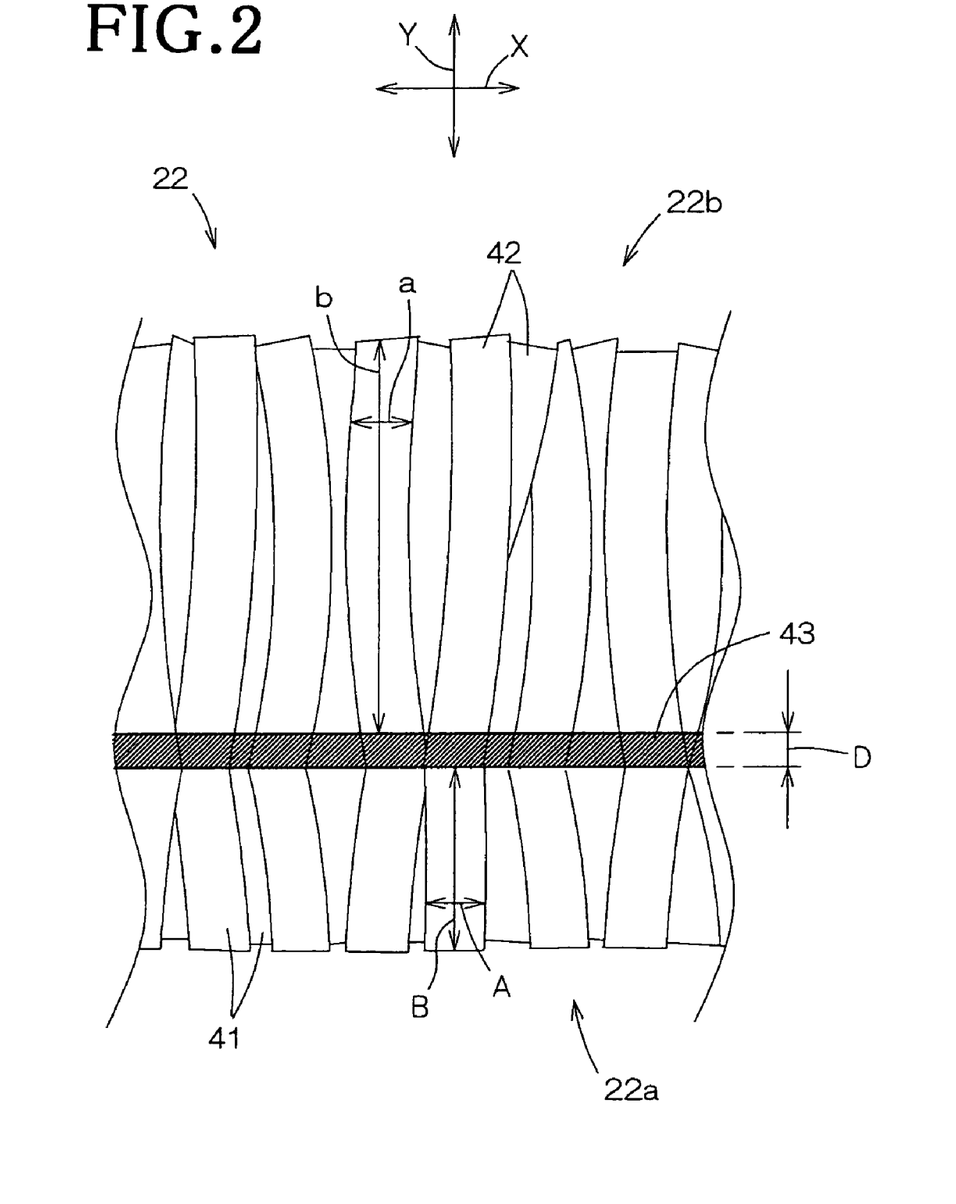
FIG. 2 is a scale-enlarged diagram illustrating a part of FIG. 1.

FIG. 2 is a scale-enlarged diagram illustrating a part of the barrier 22. Each of the strips 41 forming the front barrier 22a has a width A as measured in the transverse direction X and a length B as measured in the back-and-forth direction Y while each of the strips 42 forming the rear barrier 22 b has a width a as measured in the transverse direction X and a length b as measured in the back-and-forth direction Y. The strips 41 are arranged side by side in the transverse direction X and the strips 42 also are arranged side by side in the transverse direction X. These strips 41, 42 are bonded to the topsheet 2 along the welding line 43 having a width D as measured in the back-and-forth direction Y. The strips 41, 42 preferably have the respective widths A, a in a range of 3 to 15 mm, respective lengths B, b in a range of 5 to 70 mm. The welding line 43 preferably has the dimension D in a range of 1 to 5 mm. In the illustrated embodiment, the width A of the strip 41 in the front barrier 22 a is the same as the width a of the strip 42 in the rear barrier 22 b and the length B of the strip 41 is smaller than the length b of the strip 42. The welding line 43 is laid in the crotch covering region 6 at a location between the front waist covering region 7 and a centerline M-M bisecting a dimension of the diaper 1 as measured in the back-and-forth direction Y (See FIG. 1).

Figure 3:
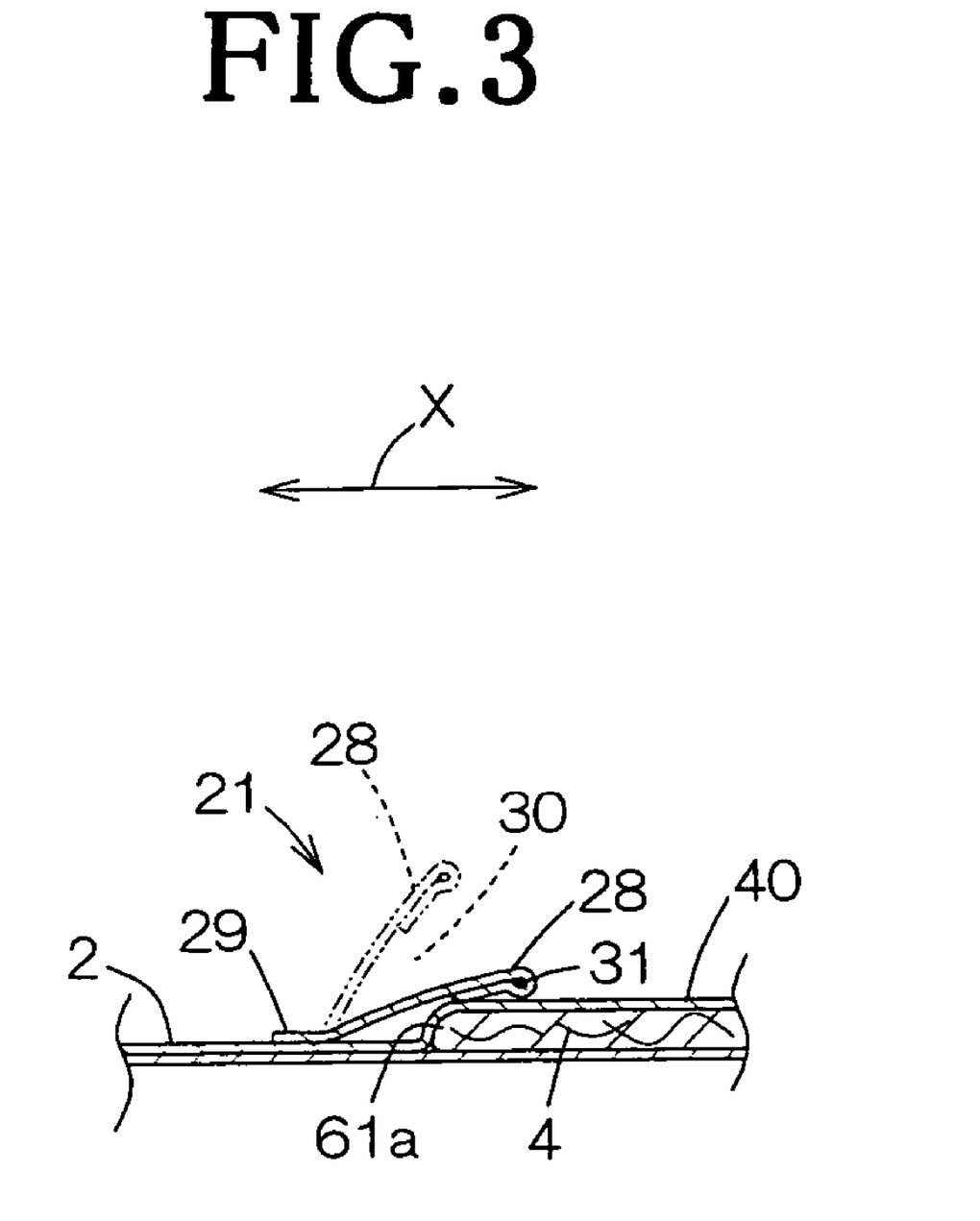
FIG. 3 is a sectional view taken along the line III-III in FIG. 1.

FIG. 3 is a sectional view taken along the line III-III in FIG. 1. As shown, the proximal side edge 29 of the leak-barrier cuff 21 is bonded to the topsheet 2 outside aside edge 61a of the core 4 by means of adhesives or a suitable welding technique. The distal side edge 28 lies inside the side edge 61a of the core 4 and above the body fluid absorbent panel 40. The elastic member 31 contracts as the diaper 1 curves in the back-and-forth direction Y, whereupon the distal side edge 28 rises up above the topsheet 2 as indicated by imaginary lines and cooperates with the topsheet 2 to open the pocket 30 toward the centerline C-C (See FIG. 1).

Figure 4:
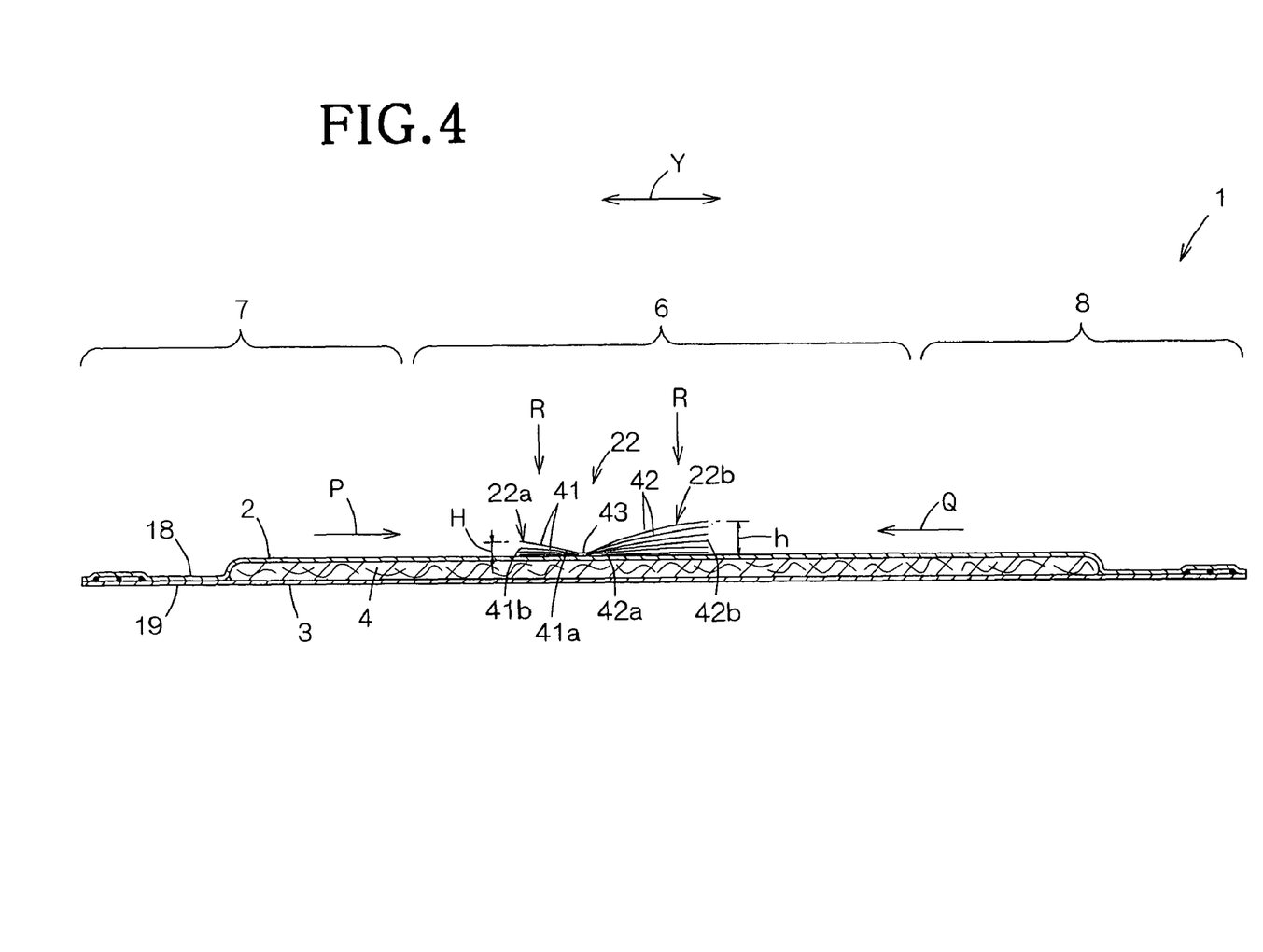
FIG. 4 is a sectional view taken along the line IV-IV in FIG. 1.

FIG. 4 is a sectional view taken along the line IV-IV in FIG. 1 wherein the line IV-IV coincides with the centerline C-C. The front barrier 22a and the rear barrier 22b respectively comprise assemblies of the strips 41, 42. In each of these assemblies, each pair of the adjacent strips 41 or 42 overlap each other in a thickness direction thereof. Along the welding line 43, each pair of the adjacent fixed ends 41a or each pair of the adjacent fixed ends 42a of the strips successively overlapping one another are welded to each other and, at least partially along the welding line 43, the fixed end 41a and the fixed end 42a which is adjacent to the fixed end 41a in the back-and-forth direction is overlapped and welded to each other. These strips 41 or 42 are gradually spaced one from another as these strips 41 or 42 extend from the respective fixed ends 41a or 42a toward the respective free ends 41b or 42b so that the front barrier 22a in its entirety and the rear barrier 22b in its entirety respectively present tufted states. Of these front and rear barriers 22a, 22b of such construction, the front barrier 22a, on one hand, is able to stand in the way of a flow P of body fluid such as urine moving on the topsheet 2 from the front waist covering region 7 toward the crotch covering region 6 which otherwise would move beyond the crotch covering region 6. Such body fluid can be guided into spaces defined among a plurality of the strips 41 and/or absorbed by the core 4 underlying these strips 41 as viewed in FIG. 4. In this way, the strips 41 are able also to prevent the body fluid from coming in direct contact with the wearer's skin with the result of contaminating the wearer's skin and/or giving the wearer's skin an uncomfortable feeling of wetness. The rear barrier 22b, on the other hand, is able to stand in the way of a flow Q of the body fluid such as loose passage moving on the topsheet 2 from the rear waist covering region 8 toward the crotch covering region 6 which otherwise would move beyond the crotch covering region 6. Such body fluid can be guided into spaces defined among a plurality of the strips 42. In this way, the strips 42 are able also to prevent such body fluid from contaminating the diaper wearer's skin. The diaper 1 including the barrier 22 can eliminate an anxiety that the body fluid such as urine flowing in the direction P and the body fluid such as loose passage flowing in the direction Q might commingle together in the crotch covering region 6 and remarkably contaminate the diaper wearer's skin.

Now it is assumed that the diaper 1 is put on the wearer's body and a body weight of the wearer is exerted on the barrier 22 in a thickness direction of the diaper 1 indicated by an arrow R. In the case of the barrier 22 functioning in the manner as has been described above, the front and rear barriers 22a, 22b which have been in tufted state are deformed, preferably in elastic manner so that heights H, h of these barriers 22a, 22b are reduced. So far as the front and rear barriers 22a, 22b are adapted to be elastically deformed, the heights H, h reduced in this manner can be substantially restored to the initial values as soon as these barriers 22a, 22b are relieved of the body weight. In other words, the strips 41, 42 forming the respective barriers 22a, 22b compressed in close contact with the wearer's crotch region immediately after the diaper 1 has been put on the wearer's body will have the free ends 41b, 42b substantially restored to the respective initial states when the crotch covering region 6 of the diaper 1 is spaced apart from the wearer's crotch region so that these free ends 41b, 42b can continue to be held in close contact with the wearer's crotch region. In this way, no significant gap is left between the skin of the wearer's crotch region and the free ends 41b, 42b of the strips 41, 42 in the crotch covering region 6. Thus it is unlikely that bodily discharges on an inner surface 18 might move through the gap between the strips 41, 42 and the wearer's skin and substantially beyond the front barrier 22a and/or the rear barrier 22b. In addition, the individual strips 41, 42 arranged side by side and forming the front barrier 22a and the rear barrier 22b, respectively, can be independently deformed without mutual restriction of the deformation between each pair of the adjacent strips. As an advantageous result, the front and rear barriers 22a, 22b comprising these strips 41, 42, respectively, can reliably come in close contact with both the protuberant spots and the depressed spots of the wearer's crotch region.

Figure 8:
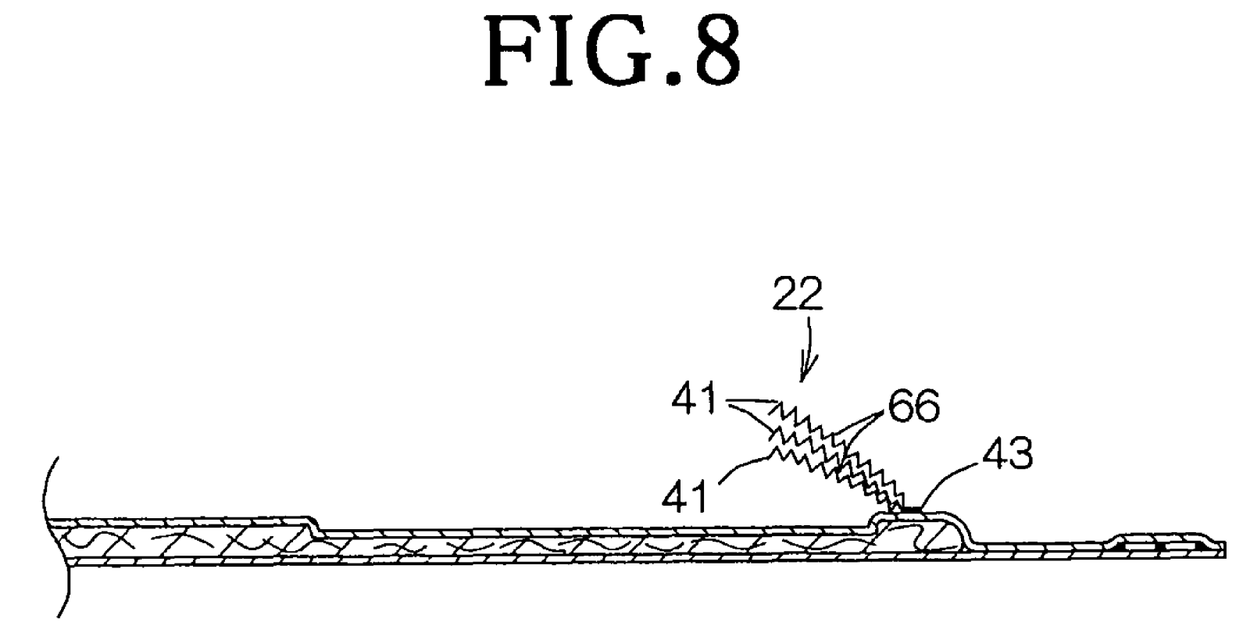
FIG. 8 is a sectional view taken along the line VIII-VIII, exemplarily showing the strips.

The strips 41, 42 constituting such elastically deformable front and rear barriers 22a, 22b are preferably formed from a bulky nonwoven fabric made of thermoplastic synthetic fibers having a basis weight in a range of 10 to 100 g/m$^2$ and a density in a range of 0.05 to 0.1 g/cm$^3$. This density of the nonwoven fabric is measured on the basis of a thickness of the nonwoven fabric under a load of 3 g/cm$^2$ and a weight per 1 cm$^2$. As the thermoplastic synthetic fibers forming the nonwoven fabric, crimped fibers such as crimped conjugate fibers is preferably used in order to facilitate the strips 41, 42 to be elastically deformed. Elastic deformation of the front and rear barriers 22a, 22b can be facilitated also by using the strips 41, 42 formed along in the longitudinal direction thereof with a plurality of folds 66 which repetitively rise and fall as illustrated in FIG. 8. While the strips 41, 42 may be made of either a hydrophilic nonwoven fabric or hydrophobic nonwoven fabric, it is preferred to use the hydrophilic nonwoven fabric. This is for the reason that, even if the wearer's skin is soiled with bodily discharges such as urine and loose passage, the strips made of the hydrophilic nonwoven fabric will scrape off such soiling which will be, in turn, transferred to the strips 41, 42. While the position of the welding line 43 for the barrier 22 is shown in FIG. 1 as put aside from the centerline M-M toward the front waist covering region 7, it is also possible to lay the welding line 43 at the position put aside toward the rear waist covering region 8. If the welding line 43 is laid in coincidence with the centerline M-M, the diaper 1 will be advantageously folded in two along the centerline M-M when the diaper 1 is packaged. More specifically, such layout of the welding line 43 is advantageous because the strips 41, 42 fully rise as the diaper 1 is unfolded in the back-and-forth direction Y and the front and rear barriers 22a, 22b having the maximum values of the heights H, h are obtained.

While the barrier 22 shown in FIGS. 1 through 4 comprises the front and rear barriers 22a, 22b, it is possible for the barrier 22 to comprise only one of these two barriers 22a, 22b without departing from the scope of the invention. The invention may be exploited in the form of the diaper 1 comprising none of the leak-barrier cuffs 21 with which the illustrated diaper 1 is provided. In the illustrated diaper 1, materials for the topsheet 2 may be selected from the group consisting of a nonwoven fabric, liquid-pervious perforated thermoplastic synthetic resin film and the like. Materials for the backsheet 3 may be selected from the group consisting of a thermoplastic synthetic resin film, a laminate sheet formed from thermoplastic synthetic resin film and nonwoven fabric, and the like. The core 4 may be provided in the form of a block of body fluid absorbent material, for example, comprising fluff pulp or a mixture of fluff pulp and super-absorbent polymer particles or such block wrapped with a liquid-diffusible and -pervious sheet such as a tissue paper.

Figure 5:
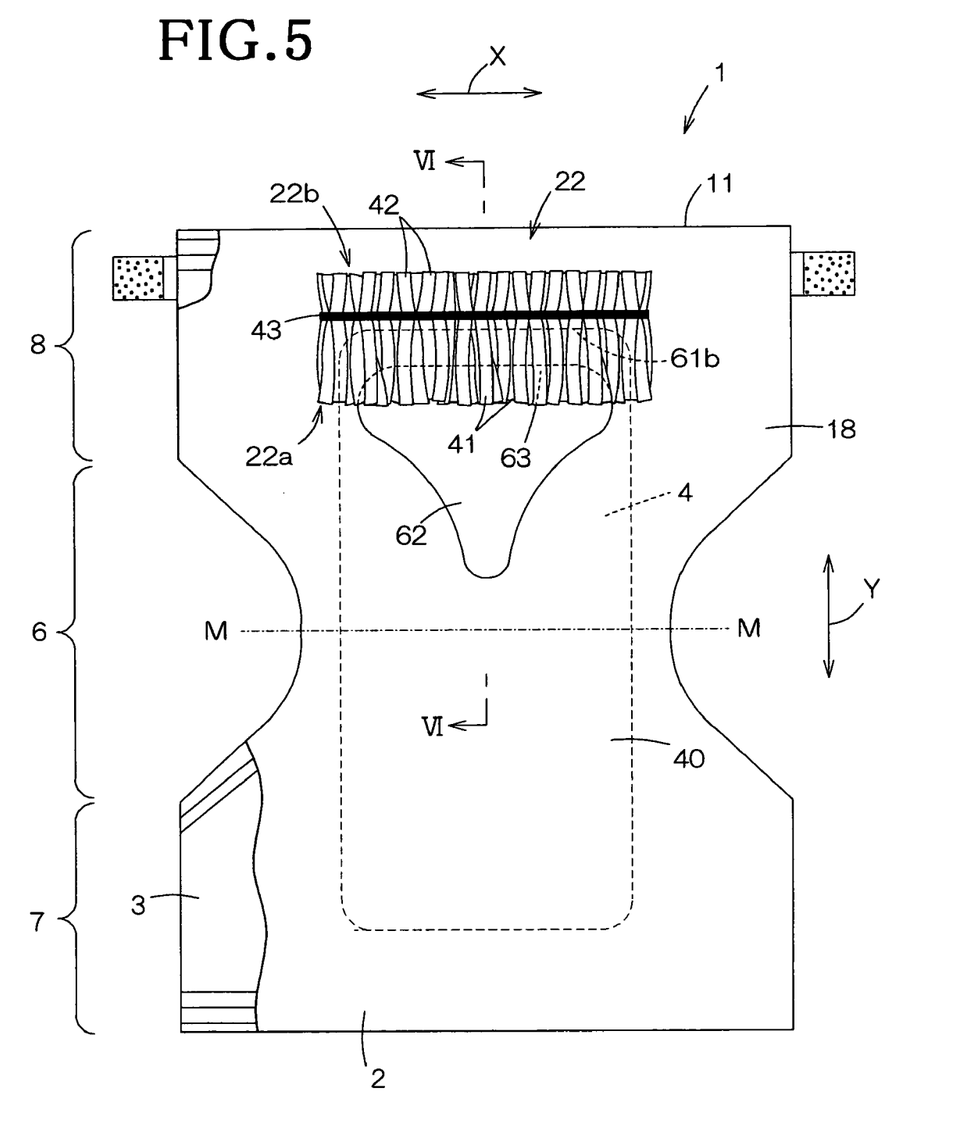
FIG. 5 is a view similar to FIG. 1, showing one preferred embodiment of the invention.
Figure 6:
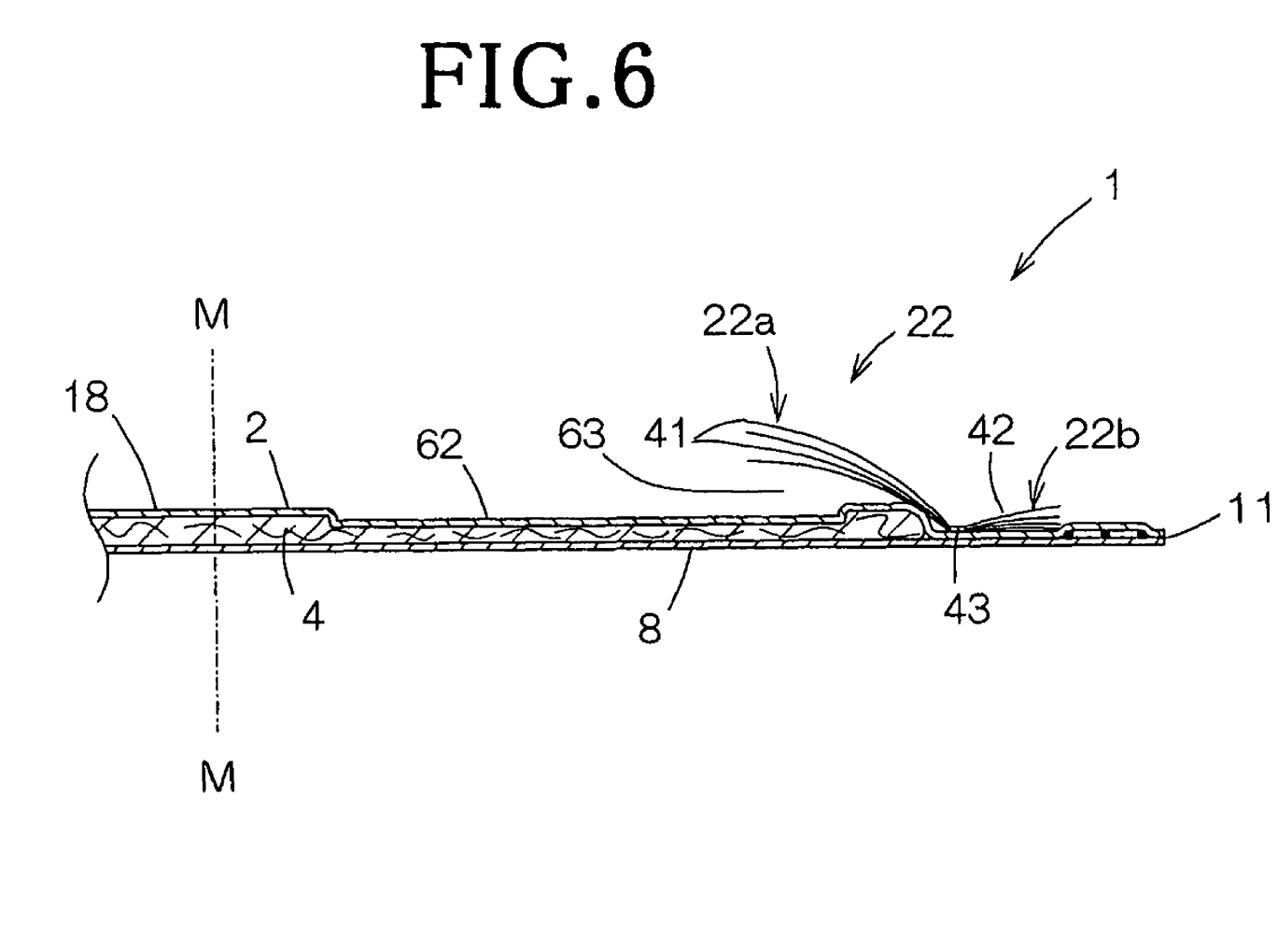
FIG. 6 is a sectional view taken along the line VI-VI in FIG. 5.

FIG. 5 is a view similar to FIG. 1, showing one preferred embodiment of the invention and FIG. 6 is a sectional view taken along the line VI-VI in FIG. 5. In the diaper 1 of FIGS. 5 and 6, the barrier 22 is laid in the rear waist covering region 8 and the welding line 43 is laid between the end 11 of the rear waist covering region 8 and the end 61b of the core 4 and extends in the transverse direction X. The front barrier 22a making a part of the barrier 22 has the strips 41 extending from the welding line 43 beyond the end 61b of the core 4 toward the centerline M-M. The rear barrier 22b making another part of the barrier 22 has the strips 42 extending from the welding line 43 toward the end 11 of the rear waist covering region 8. The body fluid absorbent panel 40 comprising the core 4 and top- and backsheets 2, 3 sandwiching the core 4 is formed with a feces retaining depression 62 extending over the crotch covering region 6 and the rear waist covering region 7. The depression 62 has a generally inverted triangle shape. The depression 62 is formed on the inner surface 18 so that the thickness of the core 4 is smaller in the depression 62 than outside the depression 62. The strips 41 of the front barrier 22a partially cover the depression 62 and thereby cooperate with this depression 62 to form a pocket 63 opening toward the centerline M-M. With such diaper 1, loose passage moving on the side of the wearer's back flows first into the depression 62 and then into the pocket 63. In this way, leakage of loose passage beyond the end 11 of the rear waist covering region 8 can be prevented. The pocket 63 including the depression 62 is not readily closed even if the body weight is exerted on the front barrier 22a from above as viewed in FIG. 6 and therefore movement of loose passage toward the end 11 can be reliably held back. The welding line 43 lying down between the tufted front and rear barriers 22a, 22b as seen in FIG. 6 is held to be spaced from the wearer's skin during use of the diaper 1. If it is accepted that the welding line 43 comes in contact with the wearer's skin during use of the diaper 1, the rear barrier 22b functioning as has been described above may be omitted. In view of the fact that the depression 62 is not essential to the diaper 1, this depression 62 may be omitted without departing from the scope of the invention. Furthermore, it is also possible without departing from the scope of the invention to provide the barrier 22 in the front waist covering region 7.

Figure 7:
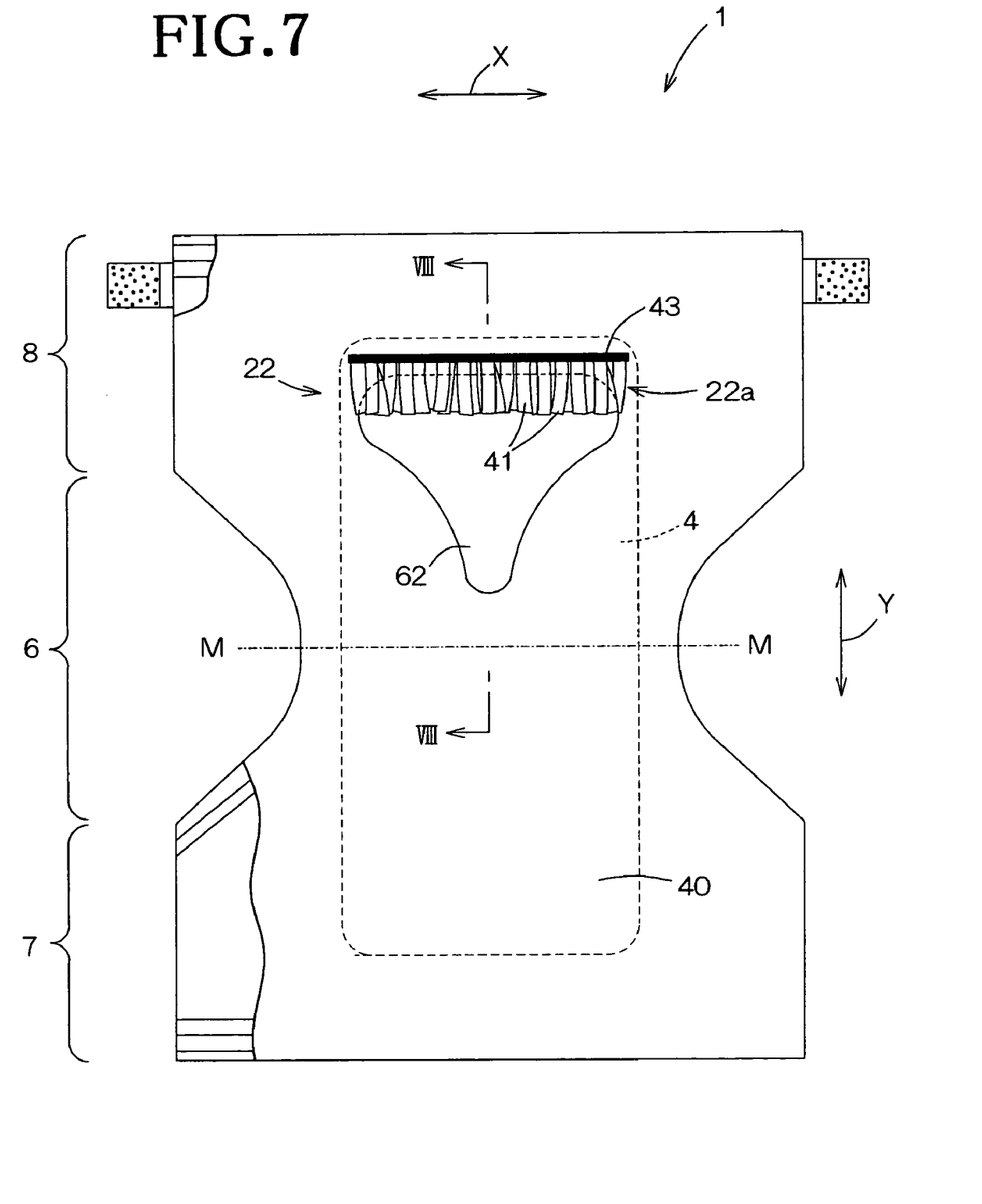
FIG. 7 is a view similar to FIG. 5, showing another preferred embodiment of the invention.

FIG. 7 is a view similar to FIG. 5, showing another preferred embodiment of the invention. The barrier 22 in this diaper 1 includes the front barrier 22a extending forward from the welding line 43 but the rear barrier 22b extending rearward from the welding line 43 is omitted. In this embodiment, the welding line 43 is disposed on the topsheet 2 over a partial width of the topsheet 2 defined by the its portion immediately overlying the core 4. Each of the strips 41 presents a substantially same shape as the strip 41 of the front barrier 22a in the embodiment shown in FIG. 5.

FIG. 8 is a sectional view taken along the line VIII-VIII in FIG. 7, exemplarily showing the strips 41 used in the embodiment as illustrated in FIG. 7. Each of the strips 41 is made of a nonwoven fabric and formed along its longitudinal direction with a plurality of folds 66 which are repetitively rise and fall. Even if the nonwoven fabric forming these strips 41 is of inelastic nature, the presence of the folds 66 allows the strips 41 to be elastically deformed and facilitates the assembly of these strips 41 to form the tufted barrier 22. It is possible to use the strips 41 each having such folds 66 for the diaper 1 according to the embodiment shown in FIG. 1.

This invention is not limited to the illustrated embodiments and may be exploited in the form of the diaper having the barriers 22 in the crotch covering region 6, the front waist covering region 7 and the rear waist covering region 8, respectively.

This invention allows production of the diaper having the barrier adapted to prevent body fluid from freely moving in the back-and-forth direction of the diaper and adapted to be held in close contact with the wearer's skin.

What is claimed is:

1. A disposable diaper having a longitudinal direction and a transverse direction which is orthogonal to said longitudinal direction, said diaper comprising:
   a front waist region;
   a rear waist region;
   a crotch region extending in said longitudinal direction between said front and rear waist regions;
   a body fluid absorbent panel at least partially wrapped with a liquid-pervious sheet and extending over said crotch region and into said front waist region and said rear waist region, said liquid-pervious sheet being directly contactable with a wearer's body, in use;
   a barrier in at least one of (a) said crotch region, (b) said front waist region and (c) said rear waist region, said barrier extending in said transverse direction so as to stand, in use, in the way of body fluid flowing on said liquid-pervious sheet in said longitudinal direction;
   said barrier being formed from a tufted assembly comprising a plurality of nonwoven fabric strips each having a width and a length orthogonal to each other,
   wherein said plurality of strips are arranged side by side with respective said widths being in alignment in said transverse direction so that said strips successively overlap one another along respective said lengths as viewed in a thickness direction of said diaper, and
   wherein each of said strips has, as viewed in said longitudinal direction of said diaper, opposite front and rear end portions which are free of direct attachment to said liquid-pervious sheet and to other strips, and
   a middle portion which extends between said front and rear end portions and is directly fixed to at least one of (i) said liquid-pervious sheet and (ii) the middle portion of at least one overlying or underlying strip;
   said end portions projecting away from the liquid-pervious sheet in the thickness direction of the diaper, and being elastically deformable by the wearer's body, in use, to ensure direct close contact between some of said end portions and the wearer's body, in use;
wherein said barrier comprises a rear barrier defined by the rear end portions of said strips, which extend from said middle portions toward said rear waist region, and a front barrier defined by the front end portions of said strips, which extend from said middle portions toward said front waist region;
wherein
the front end portions of said overlapping strips are arranged in several layers, as seen in the thickness direction of the diaper, on top of the liquid-pervious sheet, and project at various angles and heights away from the respective middle portions toward the front waist region to define the front barrier which is continuous in the transverse direction over a full width of said absorbent panel and which has a substantial constant height, in the thickness direction, throughout its length in the transverse direction;
the rear end portions of said overlapping strips are arranged in several layers, as seen in the thickness direction of the diaper, on top of the liquid-pervious sheet, and project at various angles and heights away from the respective middle portions toward the rear waist region to define the rear barrier which is continuous in the transverse direction over the full width of said absorbent panel and which has a substantial constant height, in the thickness direction, throughout its length in the transverse direction; and
the height of the front barrier when the diaper is not in use is lower than that of the rear barrier.

2. The diaper as defined by claim 1, wherein the middle portions of all said strips in said barrier are directly bonded to said liquid-pervious sheet and/or to the middle portions of the overlaying or underlying strips along a single line extending in said transverse direction and positioned closer to said front waist region than to said rear waist region.

3. The diaper as defined by claim 1, wherein said nonwoven fabric contains crimped fiber.

4. The diaper as defined in claim 1, wherein the front barrier, as measured in the longitudinal direction, is shorter than the rear barrier.

5. The diaper as defined by claim 4,
wherein the middle portions of all said strips in said barrier are directly bonded to said liquid-pervious sheet and/or to the middle portions of the overlaying or underlying strips along a single line extending in said transverse direction and positioned closer to said front waist region than to said rear waist region.

6. The diaper as defined by claim 5, having a single said barrier.

7. The diaper as defined by claim 1, wherein said overlapping strips are monolithic strips arranged in several layers, as seen in the thickness direction of the diaper, on top of the liquid-pervious sheet, and projecting at various angles and heights away from said liquid-pervious sheet.

8. A disposable diaper having a longitudinal direction and a transverse direction which is orthogonal to said longitudinal direction, said diaper comprising:
a front waist region, a rear waist region, and a crotch region extending in said longitudinal direction between said front and rear waist regions;
a body fluid absorbent panel at least partially wrapped with a liquid-pervious sheet and extending over said crotch region and into said front waist region and said rear waist region, said liquid-pervious sheet being directly contactable with a wearer's body, in use;
a barrier in at least one of (a) said crotch region, (b) said front waist region and (c) said rear waist region, said barrier having a dimension in the transverse direction greater than in the longitudinal direction so as to stand, in use, in the way of body fluid flowing on said liquid-pervious sheet in said longitudinal direction;
said barrier being formed from a tufted assembly comprising a plurality of monolithic nonwoven fabric strips each having a width in the transverse direction and a length in the longitudinal direction;
wherein
said strips are arranged side by side and overlap each other in the longitudinal and transverse directions as well as a thickness direction of the diaper to define several layers of said strips on top of the liquid-pervious sheet;
each of said strips has
a fixed portion, which is directly fixed to at least one of (i) said liquid-pervious sheet and (ii) the fixed portion of at least one overlying or underlying strip, and
a free portion, which is free of direct attachment to said liquid-pervious sheet and to other strips;
said free portions project obliquely upward, in the thickness direction of the diaper, and at various angles and heights away from the liquid-pervious sheet and towards one of said front and rear waist regions; and
said free portions are elastically deformable by the wearer's body, in use, to ensure close direct contact between some of said free portions and the wearer's body, in use.

9. The diaper as defined by claim 8, wherein the fixed portions of all said strips in said barrier are directly bonded to said liquid-pervious sheet and/or to the fixed portions of the overlaying or underlying strips along a single line extending in said transverse direction.

10. The diaper as defined by claim 9, wherein
said single line is positioned in the crotch region and closer to the front waist region than to the rear waist region; and
said free portions project obliquely upward from said single line and towards said rear waist region.

11. The diaper as defined by claim 9, having a single said barrier.

12. The diaper as defined by claim 9, wherein said nonwoven fabric contains crimped fibers which render said strips elastically deformable.

13. The diaper as defined by claim 8, wherein
the fixed portions of all said strips in said barrier are directly bonded to said liquid-pervious sheet and/or to the fixed portions of the overlaying or underlying strips along a single line extending in said transverse direction;
the free portions of all said overlapping strips are arranged in several layers, as seen in the thickness direction of the diaper, on top of the liquid-pervious sheet, and project at various angles and heights away from said single line toward said one of the front and waist regions to define the barrier which is continuous in the transverse direction over a full width of said absorbent panel.

14. The diaper as defined by claim 8, wherein
the front end portions of said overlapping strips terminate at edges that point towards the front waist region; and
the rear end portions of said overlapping strips terminate at edges that point towards the rear waist region.

15. The diaper as defined by claim 8, wherein some of said free portions are not directly contactable with the wearer's body, in use.

* * * * *